United States Patent [19]

Barker et al.

[11] Patent Number: 4,900,513

[45] Date of Patent: Feb. 13, 1990

[54] SAMPLE LOADING APPARATUS

[75] Inventors: Stephen F. Barker, Pomona; Harold F. Fechtner, Claremont, both of Calif.

[73] Assignee: Beckman Instruments, Inc., Fullerton, Calif.

[21] Appl. No.: 373,690

[22] Filed: Jul. 3, 1989

Related U.S. Application Data

[63] Continuation of Ser. No. 132,720, Dec. 11, 1987, abandoned, which is a continuation of Ser. No. 884,463, Jul. 11, 1986, abandoned.

[51] Int. Cl.[4] .......................................... G01N 35/04
[52] U.S. Cl. ..................................... 422/64; 422/63; 198/346.1; 198/465.2
[58] Field of Search ................................. 422/63–67, 422/72, 73; 436/43–48; 198/346.1, 365.1, 365.2; 414/31, 34, 45, 47, 222

[56] References Cited

U.S. PATENT DOCUMENTS

| | | | |
|---|---|---|---|
| 3,589,867 | 6/1971 | Heinz et al. | |
| 3,605,829 | 9/1971 | Genese et al. | 141/79 |
| 3,644,095 | 2/1972 | Netheler et al. | 422/65 |
| 3,917,455 | 11/1975 | Bak et al. | 23/253 |
| 3,951,609 | 4/1976 | Palenscar | 23/259 |
| 4,113,436 | 9/1978 | Werder et al. | 422/65 |
| 4,268,477 | 5/1981 | Herzstark | 422/64 |
| 4,287,155 | 9/1981 | Tersteez et al. | 422/64 |
| 4,296,069 | 10/1981 | Smith et al. | 422/64 |
| 4,296,070 | 10/1981 | Montalto et al. | 422/64 |
| 4,298,571 | 11/1981 | DiFulvio et al. | 422/64 |
| 4,322,216 | 3/1982 | Lillig et al. | 23/230 |
| 4,443,147 | 4/1984 | Richards | 414/47 |
| 4,480,738 | 11/1984 | Mattson | 198/465.1 |
| 4,528,159 | 7/1985 | Liston | 422/64 |
| 4,588,343 | 5/1986 | Garrett | 414/222 |
| 4,595,562 | 6/1986 | Liston et al. | 422/65 |

Primary Examiner—Michael S. Marcus
Attorney, Agent, or Firm—William H. May; Arnold Grant; Gary T. Hampson

[57] ABSTRACT

A sample loading and unloading apparatus for an automated clinical instrument including a loading tray adapted to receive a plurality of sample carrying sectors. The apparatus further includes a sample carousel having a plurality of locations each adapted to receive sample sectors. The portion of the sample carousel nearest the loading tray defines a transfer position. The loading tray includes a transfer assembly for transferring a sector positioned at the transfer position from the sample carousel to the loading tray and simultaneously transferring a sector from the loading tray to the sample carousel. The transfer assembly includes a transfer spider which may be pneumatically raised to temporarily lift the sample sectors from the loading tray and the sample sector from the transfer position. The transfer assembly is rotated to a next index position and is lowered to thereby transfer the sample sector from the transfer position to the loading tray, increment sample sectors around the loading tray, and transfer a sector from a loading position on the loading tray to the transfer position.

18 Claims, 1 Drawing Sheet

SAMPLE LOADING APPARATUS

This is a continuation of copending application Ser. No. 132,720, filed on Dec. 11, 1987, abandoned, which is a continuation of co-pending application Ser. No. 06/884,463 filed July 11, 1986, now abandoned.

FIELD OF THE INVENTION

The present invention relates to the field of automated clinical analyzers and more particularly to a sample loading and unloading apparatus for use in and with such analyzers.

BACKGROUND OF THE INVENTION

Automated clinical analyzers are used in clinical chemistry laboratories to automatically process patient samples, determining the presence and/or concentration of various analytes in such samples. The degree of automation of such analyzers varies from instruments that simply automatically measure the concentration of a single sample placed in the instrument to systems that automatically process a large number of samples loaded onto the system by an operator.

System throughput, that is, the number of samples that can be analyzed per unit time, is an important consideration is automated systems. One of the factors affecting system throughput is the manner is which samples are loaded onto the system for analysis and removed from the system once the required analysis is completed. If the system must wait while an operator loads or removes samples, system throughput can be correspondingly affected. Thus, it is known in the art to utilize some mechanism or method which reduces the amount of time that a system must wait while an operator loads and unloads samples.

One approach is to place a number of individual samples onto a single turntable, such as is done on the Astra ® Analyzer manufactured by Beckman Instruments Inc., Brea, Ca. The single turntable is then loaded onto the analyzer, a simple operation that helps to minimize the amount of time that the analyzer is idle. When all of the samples on the turntable have been analyzed, the entire turntable can be removed and replaced with another turntable holding samples requiring analysis. Although this technique has been found to be effective, it does require that the entire sample turntable be placed onto or removed from the analyzer at one time, regardless of the number of samples that are on the turntable. Thus, the amount of time that the analyzer operation is interrupted to load a turntable is the same whether or not the turntable is filled or has only a few samples.

Another approach is illustrated by the Paramax ® Analytical System from American Dade. In The Paramax system, individual sample test tubes are loaded onto a loading carousel which is in turn loaded onto the system, similar to the Astra System just described. The sample test tubes are moved by an automatic transfer mechanism onto a transfer carousel where sample volumes are withdrawn and transferred to analysis cuvettes. The sample test tubes are then moved from the transfer carousel by another automatic transfer mechanism to an unloading carousel where they may then be unloaded by the system operator.

The Paramax system suffers from the same disadvantages noted above, namely that individual samples are loaded onto a large volume carousel and the carousel is then loaded onto the system. Thus, the versatility of the system is reduced. Furthermore, the Paramax system requires two automated sample handling mechanisms, each of which must handle individual glass sample test tubes, increasing the cost and complexity of the system.

Thus there is a need for a sample loading system that overcomes the limitations described above, making it easy and quick to load samples onto an automated analyzer without interrupting analyzer operation. There is also a need for a sample loading system that allows for the easy introduction of a limited number of samples onto the analyzer without placing the samples onto a large capacity turntable or carousel.

SUMMARY OF THE INVENTION

The present invention overcomes the limitations described above, providing an adaptable, versatile, and simple sample loading system. The analyzer need not wait while sample loading or unloading is done and thus analyzer throughput is not affected.

A sample loading and unloading apparatus in accordance with the present invention includes a loading tray comprising a plurality of locations each adapted to receive a sample carrying sector. The loading tray is separate from but associated with a sample carousel which also includes a plurality of locations each adapted to receive a sample carrying sector. The portion of the sample carousel nearest the loading tray defines a transfer position. The apparatus further includes means for performing a transfer cycle including transfering a sector positioned at the transfer position from the sample carousel to the loading tray and simultaneously transfering a sector from the loading tray onto the sample carousel at the transfer postion. A transfer cycle also includes incrementing sectors on the loading tray one location about the periphery of the tray.

The apparatus may further include means for removeably securing the sectors positioned on the loading tray and the sector positioned at the transfer position to a transfer member and means for elevating and rotating the transfer member. The means for elevating and rotating the transfer member may include a pneumatic piston within a cylinder and a motor for rotating the transfer member.

DETAILED DESCRIPTION

Figure 1:
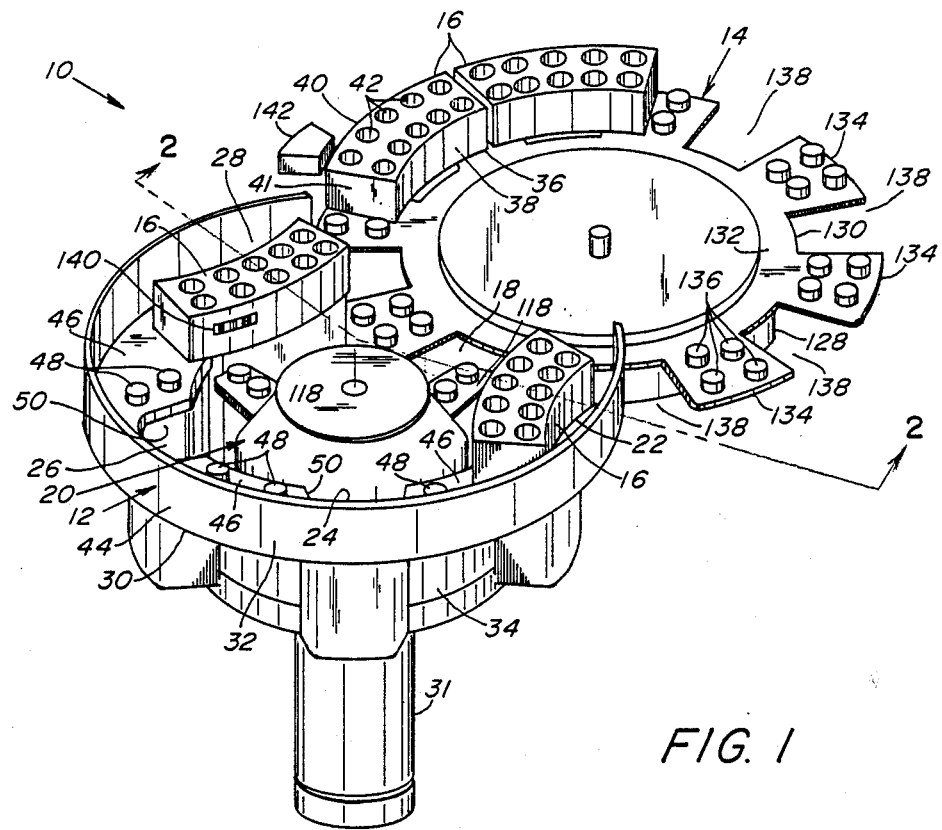
FIG. 1 is a perspective view of a sample loading apparatus in accordance with the present invention.

With reference to FIG. 1 a sample loading apparatus 10 in accordance with the present invention may be carried by an automated clinical analyzer of the type known in the art and includes a loading tray 12 and a sample carousel 14. Briefly, the loading tray 12 is adapted to receive and carry four sample carrying sectors 16 and the sample carousel 14 is adapted to receive and carry eight sample sectors 16. The portion of the sample carousel 14 nearest the loading tray 12 is defined as a transfer position 18.

The loading tray 12 includes a transfer assembly 20. The transfer assembly 20 lifts the sample sector 16 disposed at the transfer position 18 and all of the sample sectors 16 disposed on the loading tray 12 up above other sample sectors 16 disposed on the sample carousel 14. With the sample sectors 16 lifted, the transfer assembly 20 rotates the sample sectors 16 one position clockwise as seen in FIG. 1. Thus, the sample sector 16 disposed at the transfer position 18 moves to a first loading position 22, the sample sectors 16 disposed at second and third loading positions 24 and 26 are incremented one loading position clockwise about the periphery of the loading tray 12, and the sample sector 16 disposed at a fourth loading position 28 moves to the transfer position 18. The transfer assembly 20 then lowers the sample sectors 16 onto the loading tray 12 and the sample sector 16 at the loading position 18 onto the sample carousel 14.

The sample carousel 14 may rotate while sample sectors 16 are being placed onto and removed from the loading tray 12 by the analyzer operator. Also, the load/unload or transfer cycle just described can be timed to occur during a portion of the automated analyzer operating cycle that does not require rotation of the sample carousel or access to samples carried by the sector 16 positioned at the transfer position 18. Both of these factors enable the apparatus 10 to enhance analyzer throughput.

Turning now to a more detailed description of the apparatus 10, the loading tray 12 includes a housing generally designated 30 and a support tube 31. The housing 30 includes an upper portion 32 adapted to receive and support four sample sectors 16 and a lower portion 34 adapted to accommodate the transfer assembly 20 in its retracted or lowered position. The upper portion 32 defines the first through fourth loading positions 22-28 spaced around the periphery of the upper portion 32.

In the embodiment disclosed herein, each of the sample sectors 16 includes an arcuate body 36 including a first arcuate vertical surface 38, a second longer arcuate vertical surface 40, and vertical end surfaces 41 connecting the surfaces 38 and 40. As so configured, the arcuate bodies 36 of eight sample sectors 16, when placed about the periphery of the sample carousel 14, form a segmented annular assembly. Each of the sample sectors 16 includes ten openings 42 formed vertically therethrough parallel to the first and second arcuate surfaces 38 and 40. The openings 42 are adapted to receive sample cups (not shown) which in turn are adapted to receive fluid samples. The openings 42 are arranged in two arcuate rows of five openings 42 each, a first row thereof nearest to the first arcuate surface 38 and a second row thereof nearest to the second arcuate surface 40.

Figure 2:
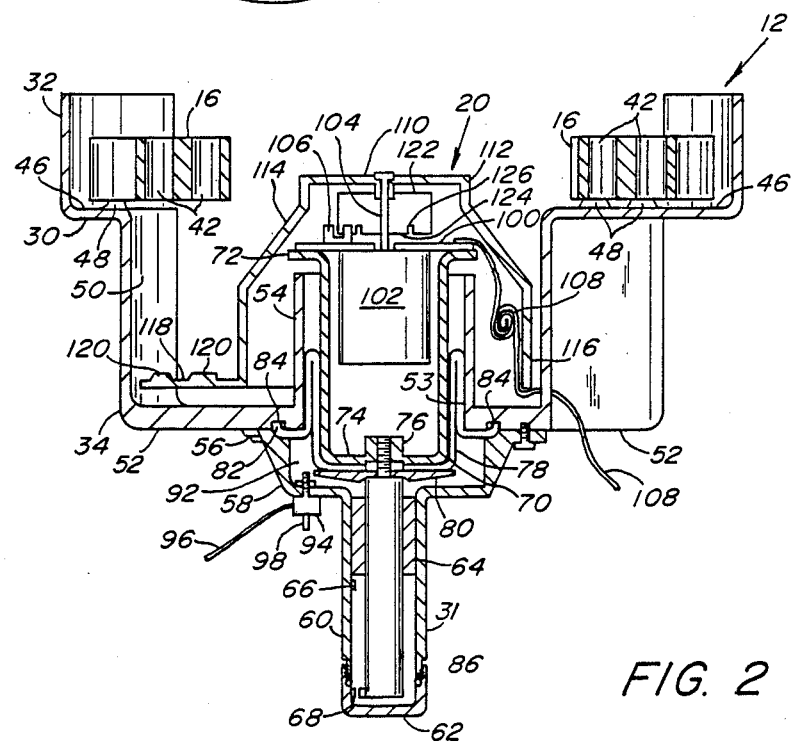
FIG. 2 is a cross-section view of the apparatus of FIG. 1 taken along the section planes 2—2 thereof.

Continuing now with the loading tray 12, the upper portion 32 thereof includes a vertical wall 44 (FIGS. 1 and 2) extending around approximately three-quarters of the periphery of the upper portion 32. The wall 44 extends slightly above the top of sample sectors 16 disposed on the loading tray 12. Five horizontal platforms 46 are formed at the base of the wall 44, the platforms 46 extending inwardly toward the center of the loading tray 12. The platforms 46 provide support surfaces for sample sectors 16 disposed within the loading tray 12 at loading positions 22-28. More particularly, each of the loading positions 22-28 includes two platforms 46 upon which the opposite ends of a sector 16 may rest. Furthermore, the platforms 46 include cylindrical upward projections 48 adapted to engage the openings 42 at both ends of sectors 16 disposed in the loading positions 22-28.

The lower portion 34 of the housing 30 is formed to define wells 50 between adjacent ones of the projections 48. The tops of the wells 50 define openings in each of the loading positions 22-28 beneath sample sectors 16 which may be disposed at such positions. A bottom horizontal wall 52 includes a circular opening 53 therethrough coaxially aligned with the central axis of the loading tray 12. The bottom wall 52 defines the bottoms of the wells 50. The opening 53 terminates in a vertical inner cylindrical wall 54 which extends upwardly approximately two-thirds the height of the wells 50.

The support tube 31 includes a horizontal flange 56 at the top thereof, the flange 56 being fixed to the lower surface of the bottom wall 52. The support tube 31 also includes a bell portion 58 fixed to the flange 56. The bell portion 58 extends downwardly and inwardly to join a vertical cylinder 60. The vertical cylinder 60 extends downwardly from the bell portion 58 and includes a closing bottom member 62. For example, the closing bottom member 62 may comprise a cap secured to the vertical cylinder 60 with an O-ring seal therebetween. Disposed within the vertical cylinder 60 is a linear bearing 64 near the upper end of the vertical cylinder 60 proximate the bell portion 58. Disposed immediately beneath the bearing 64 is a Hall effect magnetic detector 66. A second Hall effect detector 68 is aligned with the detector 66 and is fixed inside the vertical cylinder 60 proximate the closing bottom member 62. The detectors 68 are connected through the housing to external circuitry (not shown) which controls the apparatus 10 as is described hereinbelow.

The transfer assembly 20 includes pneumatic lifting means for providing upward and downward movement of the assembly 20. More particularly, the transfer assembly 20 includes a generally cup-shaped piston 70 having an annular outwardly extending lip 72 at the open upper end thereof. A bottom 74 of the piston 70 has a threaded boss 76 coaxially aligned with the central axis of the piston 70.

A flexible rolling seal such as a Bellofram Type ABC3-450-275-F is fixed between the piston 70 and the housing 30. The seal 78 is clamped to the bottom 74 of the piston 70 by means of a circular retainer plate 80 having a central opening therethrough aligned with the threaded opening in the boss 76. A bead 82 at the outer periphery of the seal 78 is disposed in an annular channel 84 formed into the bottom wall 52 concentric with the central axis of the loading tray 12. The bead 82 is clamped into the channel 84 between the flange 56 and the lower surface of the bottom wall 52.

A guide shaft 86, carried by the bearing 64, is disposed within the vertical cylinder 60. A threaded member 88 at the top of the guide shaft 86 is threaded into the boss 76 through the retainer plate 80, thus securing the retainer plate 80 to the bottom 74 of the piston 70. A magnet 90 is fixed at the lower end of the guide shaft 86 in alignment with the detectors 66 and 68.

The bottom wall 52, seal 78, retainer plate 80, and support tube 31 together define an enclosed air-tight cylinder or chamber 92 into which compressed air may be introduced via a valve 94. The valve 94 is a two-way electrically controlled valve which introduces compressed air delivered via a line 96 into the chamber 92 and, also under electric control, vents air within the chamber 92 to atmosphere through an outlet 98.

Fixed to the pneumatic lifting means just described is rotating means comprising a mounting plate 100 and a stepper motor 102. The mounting plate 100 is fixed atop the lip 72 and supports the stepper motor 102 within the piston 70. The stepper motor 102 includes a shaft 104 coaxially aligned with the piston 70. The mounting plate 100 also serves as an electrical connection point for the stepper motor 102 and a U-shaped position detector 106 comprising, for example, a light source and photodetector. Flexible conductors 108 connect the stepper motor 102 and detector 106 through the housing 30 to external circuitry (not shown). The external circuitry controls the stepper motor 102 in response to signals from the detector 106 as is described below.

The transfer assembly 20 also includes a transfer spider 110 affixed to the end of the stepper motor shaft 104. The upper portion of the transfer spider 100 defines a cylindrical inverted shallow cup 112. The lower outer edge of the cup 112 expands outwardly and downwardly to form a tapered portion 114. The tapered portion 114 joins to a vertical cylindrical portion 116 which terminates proximate the bottom wall 52 when the transfer assembly 20 is in its lowered or retracted position.

Five pickup members or arms 118 project horizontally outwardly from the lower edge of the cylindrical portion 116. With the transfer assembly 20 in its retracted position, four of the pickup arms 118 are disposed within the wells 50 with the fifth pickup arm 118 extending outwardly into the transfer position 18 and beneath the portion of the sample carousel 14 that carries the sample sectors 16. Each of the pickup arms 118 includes two cylindrical upward projections 120. The projections 120 are adapted to be received within the two middle or center openings 42 in sample sectors 16 positioned in the first through fourth loading positions 22-28 or in the transfer position 18.

The transfer assembly 20 also includes a position flag 122 in the form of an inverted cylindrical cup and fixed to the transfer spider 110. A lower outer edge 124 of the position flag 122 travels within the U-shaped position detector 106 and includes five notches 126. The notches 126 are detected by the detector 106 to indicate that the transfer assembly 20 is in one of five index positions wherein the pickup arms 118 are aligned with the wells 50.

With respect now to the sample carousel 14 as seen in FIG. 1, the sample carousel 14 includes a base 128 to which is rotatably affixed a support ring 130. The support ring 130 is preferably driven by a stepper motor (not shown) disposed in the base 128 and operated by control circuitry (not shown) which also operates the stepper motor 102 and the valve 94. As seen with respect to FIG. 1, a plane defined by the platforms 46 is somewhat above a plane defined by the support ring 130.

The support ring 130 comprises an inner annular member 132 and a plurality of radially projecting horizontal support arms 134. In the embodiment disclosed herein, the sample carousel 14 includes eight support arms 134. Each of the support arms 134 includes four cylindrical upward projections 136. Sample sectors 16 may be placed onto the support ring 130 such that the sectors 16 straddle adjacent support arms 134. Two projections 136 on such adjacent support arms 134 form a group of four projections 136 that fit into the openings 42 at either end of a sector 16 to thus removably retain the sector 16 on the sample carousel 14. The support arms 134 define spaces 138 therebetween which are sized slightly larger than the pickup arms 118 so that the pickup arms 118 may pass through the spaces 138. With the transfer assembly 20 in its lowered or retracted position, the pickup arms 118 and projections 120 carried thereon are disposed in a plane below the plane defined by the support ring 130.

To identify sample sectors 16 carried on the the sample carousel 14, each of the sectors 16 may include a bar coded label 140 fixed to the second arcuate surface 40. The label displays a unique serial number for the sample sector 16 and may be read by a bar code reader 142. The reader 142 is positioned outside the periphery of the support ring 130 and is aligned with the labels 140 for sample sectors 16 disposed on the support ring 130. Preferably, the output of the bar code reader is applied to the same control circuitry which controls the loading tray 12 and sample carousel 14.

In operation, the support ring 130 and any sectors 16 disposed thereon are free to rotate on the base 128 while sample sectors 16 may be removed from and placed onto the loading tray 12 at any one of the loading positions 22-28. This freedom of rotation allows the analyzer to position samples on the sample carousel 14 as needed so that sample volumes may be withdrawn for analysis. Thus, as an operator loads or removes sample sectors 16 from the loading tray 14, the sample carousel 14 may be controlled independently to maximize analyzer throughput.

The next sector 16 to be loaded onto the sample carousel 14 during a transfer cycle performed by the apparatus 10 is disposed at the fourth loading position 28. A sector may be specifically disposed at the fourth loading position 28 by the analyzer operator for immediate loading onto the sample carousel 14. The ability to easily place a sample sector 16 at the fourth loading position 28 is particularly important where such a sector carries one or more samples that are to be analyzed as soon as possible.

Before a transfer cycle is initiated, the sector 16 to be transferred from the sample carousel 14 to the loading tray 12 during the cycle is first positioned at the transfer position 18 by rotating the support ring 130. Such a sector is hereinafter referred to as the unload sector. The unload sector may be one that carries samples that have been analyzed and thus need not remain on the sample carousel 14. Preferably, the support ring 130 is rotated to position the unload sector at the transfer position 18 immediately prior to a transfer cycle so as to not interfere with analyzer operation.

The transfer cycle begins as the valve 94 is controlled to admit air into the chamber 92. As the volume of compressed air in the chamber 92 increases, the transfer assembly 20 begins to rise. As the transfer assembly 20 rises, the pick up arm 118 at the transfer position 18 first engages the unload sector 16 and then the remaining pickup arms 118 engage sample sectors 16 disposed at the loading positions 22-28.

The transfer assembly 20 completes its vertical movement with the pickup arms 118 above the tops of any sample sectors disposed on the support ring 130. The motor 102 is controlled so as to rotate the transfer spider 110 clockwise as viewed from above in FIG. 1. The rotation continues until the next notch 126 in the position flag 122 is detected by the position detector 106, indicating that the transfer spider 110 has reached the next index position. The stepper motor 102 is then deenergized and the transfer spider 110 comes to rest. The sample sector 16 that previously occupied the fourth loading position 28 is now positioned above the support ring 130 at the transfer position 18. Similarly, the unload sector 16 is now positioned above the first loading position 22 and sectors 16 previously disposed at the first through third loading positions 22-26 are positioned above the second through fourth loading positions 24-28.

The valve 94 is controlled to vent the compressed air within the chamber 92 through the outlet 98, lowering the transfer spider 110 and all sample sectors 16 carried thereby. Sample sectors first settle onto the loading tray as the pickup arms 18 fall below the platforms 46. Lastly, as the pickup arm at the transfer position 18 moves below the support ring 130, the sample sector 16 of the transfer position 18 is loaded onto the sample carousel 14.

The operation of the apparatus 10 does not require that a sample sector 16 be transferred from the tray 12 to the sample carousel 14 or that a sector 16 be transferred from the sample carousel 14 to the loading tray 12 with each cycle. For example, prior to a transfer cycle, a sample sector may be positioned at the fourth loading position 28 and there may be no sample sector 16 at the transfer position 18. After a transfer cycle as described above, the sector 16 previously located at the fourth loading position 28 is moved to the sample carousel 14 at the transfer position 18 and no sample sector 16 is then disposed at the first loading position 22. Similarly, the apparatus 10 may be used to remove a sector 16 positioned at the transfer position 18, moving such sample sector 16 to the first loading position 22, without concurrently moving a sample sector 16 from the fourth loading position 28 to the transfer position 18.

Thus, the apparatus 10 in accordance with the present invention allows sample sectors 16 to be placed onto or removed from the loading tray 12 without interrupting the operation of the associated clinical analyzer, increasing analyzer throughput. Furthermore, a transfer cycle may be performed while individual samples carried on the sample carousel are being pipetted by the automated analyzer to analysis stations, further enhancing the throughput of the analyzer.

It is to be recognized that equivalent embodiments of the present invention will be readily apparent to those skilled in the art and that the present invention is to be accorded the full scope of the claims appended hereto.

What is claimed is:

1. A sample loading and unloading apparatus for use with sample carrying sectors each adapted to carry one or more samples, the apparatus comprising:
   an at least partly circular stationary loading tray including a plurality of locations each adapted to receive a sample carrying sector;
   a sample carousel disposed proximate the loading tray and including a plurality of locations each adapted to receive a sample carrying sector, the portion of the sample carousel proximate the loading tray defining a sole transfer position; and
   means for transferring a sample carrying sector positioned at the transfer position from the sample carousel to the loading tray and simultaneously transferring a sample carrying sector from the loading tray to the transfer position on the sample carousel.

2. An apparatus as in claim 1 wherein the apparatus includes means for supporting and rotating the plurality of locations in the sample carousel.

3. An apparatus as in claim 1 wherein the transferring means comprises
   a transfer member for removably securing sectors positioned on the circular stationary loading tray and a sample carrying sector positioned at the transfer position on the sample carousel to the transfer member; and
   means for elevating the transfer member with respect to the circular stationary loading tray and sample carousel and rotating the transfer member with respect to the loading tray.

4. An apparatus as in claim 3 wherein the sample carousel locations each include carousel support members adapted to receive and support sample carrying sectors, the carousel support members defining spaces therebetween, the loading tray locations each including tray support members adapted to receive and support the sample carrying sectors, such tray support members defining spaces therebetween, and the transfer member includes arms smaller than such sample carousel spaces and such loading tray spaces, and the elevating and rotating means includes means for elevating the arms through said spaces to a position above the sample carrying sectors installed on the sample carousel.

5. An apparatus as in claim 4 wherein the means for elevating and rotating the transfer member includes a pneumatic piston, a cylinder adapted to receive the piston, and a seal therebetween.

6. An apparatus as in claim 5 wherein the means for elevating and rotating the transfer member includes means for pressurizing and depressurizing the cylinder.

7. An apparatus as in claim 3 wherein the sample carrying sectors include recesses formed therein and the loading tray platforms and sample carousel platforms, supporting the sectors, each include projections adapted to be received by such recesses.

8. An apparatus as in claim 3 wherein the apparatus includes means for indexing the rotation of the transfer member relative to the loading tray.

9. An apparatus as in claim 3 wherein transfer member rotation simultaneously increments sample carrying sectors one loading position, transfers a sample carrying sector from the loading tray to the transfer position on the sample carousel, and transfers a sample carrying sector from the sample carousel at the transfer position to the loading tray.

10. An apparatus as in claim 9 wherein the transfer member is normally below the loading tray and the sample carousel.

11. A sample loading and unloading apparatus for use with sample carrying sectors each adapted to carry one or more samples, the apparatus comprising:
    an at least partly circular stationary loading tray including a plurality of locations each adapted to receive a sample carrying sector;
    a sample carousel disposed proximate the loading tray and including a plurality of locations each adapted to receive a sample carrying sector, the portion of the sample carousel proximate the loading tray defining the sole transfer position;
    means for supporting and rotating the sample carousel;
    a transfer member comprising means for removably securing sample carrying sectors positioned on the loading tray and a sample carrying sector positioned at the transfer position on the sample carousel to the transfer member; and
    means for elevating the transfer member with respect to the loading tray and sample carousel and rotating the transfer member with respect to the loading tray.

12. A sample loading and unloading apparatus for use with sample carrying sectors each adapted to carry one or more samples, the apparatus comprising:
   an at least partly circular stationary loading tray including a plurality of locations each adapted to receive a sample carrying sector;
   a sample carousel disposed proximate the loading tray, and including a plurality of locations each adapted to receive a sample carrying sector, the portion of the sample carousel proximate the loading tray defining a sole transfer position;
   means for supporting and rotating the sample carousel;
   a transfer member including a plurality of arms extending therefrom, the arms including means for carrying sample sectors on such arms;
   means for indexing the arms in a plurality of index positions with respect to the plurality of positions included in the loading tray and with the transfer position; and
   means for supporting the transfer member with the arms in a first horizontal position beneath the plurality of locations in the loading tray and the transfer position, for elevating the transfer member from the first horizontal position to a second horizontal position with the arms above the loading tray plurality of locations and the transfer position, for rotating the transfer member from one index position to a next index position, and for lowering the transfer member to the first horizontal position.

13. A sample loading and unloading apparatus for use with sample carrying sectors each adapted to carry one or more samples, the apparatus comprising:
   a loading tray including a plurality of locations each adapted to receive a sample carrying sector;
   a rotatable sample carousel disposed proximate the loading tray and including a plurality of locations each adapted to receive a sample carrying sector, the portion of the sample carousel proximate the loading tray defining a transfer position;
   means for transferring a sample carrying sector positioned at the transfer position from the sample carousel to the loading tray and simultaneously transferring a sample carrying sector from the loading tray to the transfer position on the sample carousel; and
   the sample carousel defining a horizontal carousel plane, and the loading tray defining a horizontal loading tray plane, the horizontal loading tray plane and the sample horizontal carousel plane being different.

14. An apparatus as in claim 13 wherein the horizontal carousel plane is below the horizontal loading tray plane.

15. An apparatus as in claim 13 wherein the transfer means defines a horizontal transfer plane, the transfer plane being below the horizontal carousel plane.

16. An apparatus as in claim 13 wherein the loading tray is stationary and includes an incomplete portion of an at least partly circular periphery, the incomplete circular periphery defining the transfer position, such position extending over the horizontal carousel plane.

17. A sample loading and unloading apparatus for use with sample carrying sectors each adapted to carry one or more samples, the apparatus comprising:
   a loading tray including a plurality of locations each adapted to receive a sample carrying sector;
   a sample carousel disposed proximate the loading tray and including a plurality of locations each adapted to receive a sample carrying sector, the portion of the sample carousel proximate the loading tray defining a transfer position; and
   means for transferring a sample carrying sector positioned at the transfer position from the sample carousel to the loading tray and simultaneously transferring a sample carrying sector from the loading tray to the transfer position on the sample carousel;
   the transferring means includes a transfer member comprising means for removably securing sectors positioned on the loading tray and a sector positioned at the transfer position to the transfer member, and means for elevating the transfer member with respect to the loading tray and sample carousel and rotating the transfer member with respect to the loading tray;
   the sample carousel locations each include carousel support members adapted to receive and support the sample carrying sectors, the carousel support members defining spaces therebetween, the loading tray locations each including tray support members adapted to receive and support the sample carrying sectors, such tray support members defining spaces therebetween, and the transfer member includes arms smaller than such sample carousel spaces and such loading tray spaces, and the elevating and rotating means includes means for elevating the arms through said spaces to a position above the sample carrying sectors installed on the sample carousel; and
   the means for elevating and rotating the transfer member including a pneumatic piston, a cylinder adapted to receive the piston, and a seal therebetween.

18. An apparatus as in claim 17 wherein the means for elevating and rotating the transfer member includes means for pressuring and depressurizing the cylinder.

* * * * *